US006939311B2

(12) United States Patent
Geiger

(10) Patent No.: US 6,939,311 B2
(45) Date of Patent: Sep. 6, 2005

(54) DIAGNOSTIC ARTICLE

(75) Inventor: Wolfgang Geiger, Ansbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/776,312

(22) Filed: Feb. 12, 2004

(65) Prior Publication Data

US 2004/0176706 A1 Sep. 9, 2004

(30) Foreign Application Priority Data

Feb. 12, 2003 (DE) .......................................... 103 05 831

(51) Int. Cl.⁷ .......................... B65D 81/00; A61B 5/00
(52) U.S. Cl. ........................ 600/573; 606/185; 604/264; 600/584
(58) Field of Search ................................ 600/573, 575, 600/576, 582–584; 606/185–187; 604/20, 174, 179, 180, 239, 264, 272–274, 305, 307, 308; 2/159, 160, 161.6, 161.7

(56) References Cited

U.S. PATENT DOCUMENTS 6,123,676 A  *  9/2000 Anapliotis .................. 600/551
6,379,324 B1     4/2002 Gartstein et al.
6,706,159 B2 *   3/2004 Moerman et al. ....... 204/403.03
2002/0082543 A1 * 6/2002 Park et al. .................... 604/21
2002/0188245 A1 * 12/2002 Martin et al. ................. 604/46
2003/0009113 A1 * 1/2003 Olson ......................... 600/573
2004/0078219 A1 * 4/2004 Kaylor et al. ................. 705/2
2004/0092843 A1 * 5/2004 Kreiser et al. .............. 600/576
2004/0152957 A1 * 8/2004 Stivoric et al. ............. 600/300

FOREIGN PATENT DOCUMENTS

EP          0883371         12/1998
WO          02-017985 A2    3/2002
WO       WO 02/0 91922     11/2002

* cited by examiner

Primary Examiner—Charles Marmor
Assistant Examiner—Sadaf Toor
(74) Attorney, Agent, or Firm—Harness, Dickey & Pierce, P.L.C.

(57) ABSTRACT

A diagnostic article, in particular for medical applications, includes a microneedle array and a holding device supporting the microneedle array. The holding device is designed as a glove. The diagnostic article further includes a data recording device connected to the microneedle array, a data evaluation device connected to the data recording device, and a display device arranged on the holding device and connected to the data evaluation device.

18 Claims, 1 Drawing Sheet

DIAGNOSTIC ARTICLE

The present application hereby claims priority under 35 U.S.C. §119 on German patent application number DE 103 05 831.1 filed Feb. 12, 2003, the entire contents of which are hereby incorporated herein by reference.

FIELD OF THE INVENTION

The invention generally relates to a diagnostic article. In particular it relates to one for medical applications, preferably including a microneedle array.

BACKGROUND OF THE INVENTION

A diagnostic article is known, for example, from U.S. Pat. No. 6,379,324 B1.

A microneedle array is known from WO 02/17985 A2, for example. This microneedle array is produced by etching processes and has individual hollow needles with an internal diameter of typically 20 $\mu$m and a length of typically 0.5 mm. Such a microneedle array is intended to transport a fluid through a dermal barrier in medical applications. For example, a medicament can be administered in this way, or a blood sample collected. The advantage of the microneedle array is intended in particular to be that it is painless to use.

The microneedle array known from U.S. Pat. No. 6,379,324 is part of what is called a closed-loop system. In this case, different microneedle arrays are used for collecting samples, for delivering medication, and also as an electrode arrangement. Further, both hollow and solid microneedles are employed.

A further medical application of microneedle arrays is known from WO 02/091922. A so-called microneedle strip includes, in addition to the microneedle array, a fluid channel and a diaphragm pump.

SUMMARY OF THE INVENTION

An object of an embodiment of the invention is to make available a diagnostic article which exploits the properties of a microneedle array in a particularly advantageous manner.

According to an embodiment of the invention, an object may be achieved by a diagnostic article. This diagnostic article may include a microneedle array which is supported by a holding device, namely a so-called diagnostic glove, or is an integral part of such a holding device. The holding device does not necessarily have to have five fingers or a closed form. In any event, the holding device can be worn in a simple and comfortable manner by the user.

The microneedle array is preferably designed as a disposable component which is discarded after each analysis. The microneedles are able to take up a fluid, for example blood, and forward it, for example by capillary forces, when the microneedle array is pressed onto the sample. Only very small sample volumes are needed here.

Integrated in the microneedle array and/or the holding device there is a fluid system with which the sample can be prepared, derivatized, and delivered to a detection unit likewise integrated in the microneedle array and/or in the holding device, which detection unit permits a measurement. The measurement results obtained in this way are processed and stored in a data evaluation device, or so-called data module, which is connected to the detection unit also designated as data recording device, and/or are conveyed for storage from the data module to an additional module or a higher-ranking data system. The data module can be an integral part of the holding device designed as diagnostic glove, or can be connected mechanically to the holding device, or can be a part of the diagnostic article withdrawn from the holding device.

A display device on the holding device is also connected to the data module. The holding device may be designed as one piece, and support both the microneedle field and the display device. Alternatively, it can be designed in a number of pieces. As such, a first part can include the microneedle array, and a second part can be connected, not necessarily mechanically, to the first part and can include the display device. In any event, the display device can, like the microneedle array, be easily worn by the user, for example on the hand.

According to a particularly advantageous development, the data module can be connected by a data link to a dosing unit. When an examination, in particular a blood examination, of a patient is performed by use of the microneedle array, the dosing unit allows a medicament to be administered to the patient in a precisely dosed quantity. This occurs as a function of the test results obtained with the aid of the microneedle array. In this way, a closed-loop system is produced.

The diagnostic article is particularly suitable for association with an electronic patient record. The electronic patient record can in this case be stored in the diagnostic article itself, particularly in the data module. Alternatively, a data link can simply be provided to an electronic patient record managed in an external system. This permits an immediate or at least almost contemporaneous comparison of the data obtained with the diagnostic article and the data stored in the electronic patient record.

BRIEF DESCRIPTION OF THE DRAWINGS

The present invention will become more fully understood from the detailed description of preferred embodiments given hereinbelow and the accompanying drawings, which are given by way of illustration only and thus are not limitative of the present invention.

An illustrative embodiment of the invention is explained in more detail below with reference to diagrammatic figures, wherein.

DETAILED DESCRIPTION OF THE PREFERRED EMBODIMENTS

Figure 1:
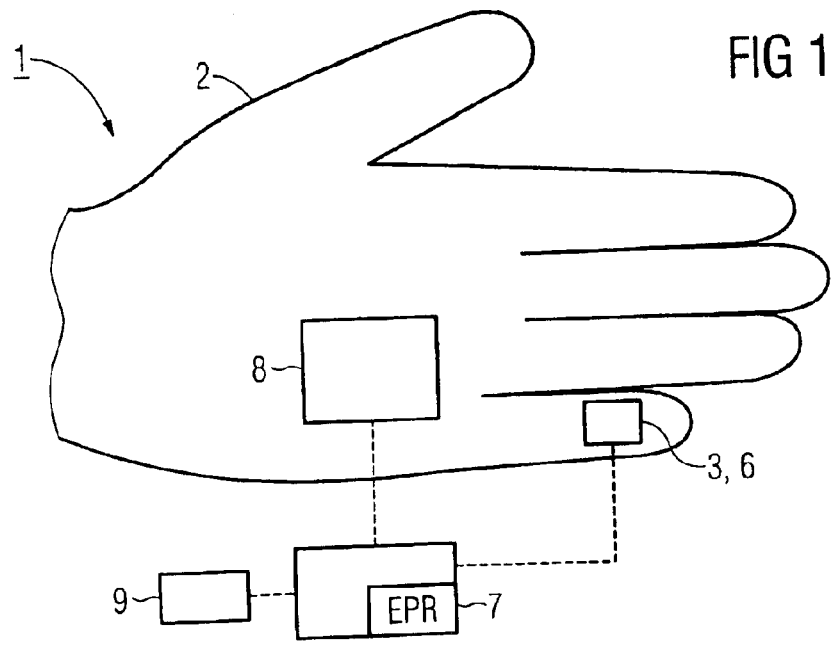
FIG. 1 shows a diagnostic article with a microneedle array, a data module, and a display device.
Figure 2:
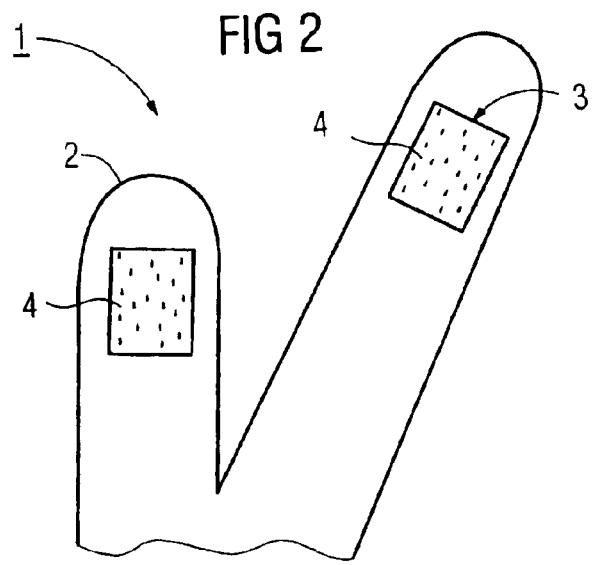
FIGS. 2 and 3 show details of the diagnostic article according to FIG. 1.
Figure 3:
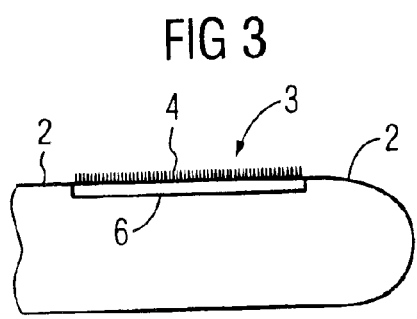

FIG. 1 shows a diagnostic article 1 with a diagnostic and analysis glove, referred to in short as a diagnostic glove, generally designated as holding device 2. A microneedle array 3 is secured on at least one finger of the diagnostic glove 2. The microneedle array 3 has a multiplicity of microneedles 4 which, as can be seen from FIG. 2 and in particular from FIG. 3, are directed outward.

In the illustrative embodiment shown, the diagnostic glove 2 is thus not intended for examining blood from the person wearing the diagnostic glove 2. Rather, with a microneedle array 3 arranged for example on the tip of the thumb and on the tip of the index finger of the diagnostic glove 2, a blood sample can be collected from a suitably perfused part of the body of a patient or animal. However, the diagnostic glove 2 can also be used, for example, to examine a transplant organ or a food specimen, for example a piece of meat or cheese. According to an alternative embodiment, the microneedles 4 in the diagnostic glove 2 are directed inward, so that the blood of the person wearing the diagnostic glove 2 can be examined.

Figure 4:
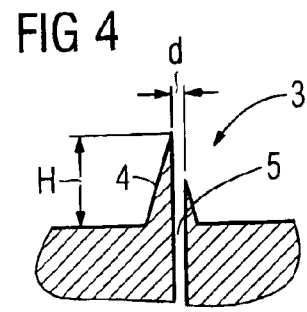
FIG. 4 shows a cross section through a microneedle of the diagnostic article according to FIG. 1.

An individual microneedle 4 shown in cross section in FIG. 4 has a height H of not more than 2 mm, in particular not more than 0.5 mm. A fluid channel 5 within the microneedle 4 has a diameter d of approximately 20 μm to 150 μm. A multiplicity of microneedles 4 are arranged in a matrix formation within the microneedle array 3.

The geometry of the microneedles 4 makes it possible to take blood from a patient or to deliver medicaments through the dermal barrier practically without pain. The microneedles 4 are designed to convey a collected sample, in particular a blood sample, through the fluid channel 5 to a detection article 6 which, in the illustrative embodiment, is designed integrally with the microneedle array 3 and with this forms an analysis chip.

The detection article 6, also designated as data recording device, is connected via a data link, indicated by a broken line in FIG. 1, to a data module 7 also designated as data evaluation device. In the illustrative embodiment, the data module 7 is arranged outside the holding device 2. However, it can also be integrated into the holding device 2 or into the detection article 6. The data link between the detection article 6 and the data module 7 can be produced, for example, by way of a cable or by way of a wireless connection, for example a radio connection.

In cases where data have been determined on examining a patient, the data module 7 serves to transmit the data obtained with the aid of the microneedle array 3 to an electronic patient record EPR. The electronic patient record EPR can either be stored in the data module 7, as indicated in FIG. 1, or in a higher-ranking data system to which the data module 7 is linked. The data module 7 can likewise be realized in software form in a data processing system.

The data processed in the data module 7 and derived from the measurements carried out with the aid of the microneedle array 3 are compared with the data present in the electronic patient record EPR, in particular the individual data concerning the patient. The result of this measurement can, for example, trigger a follow-up measurement, either again via the microneedle array 3 or via another system not shown.

To display data obtained with the aid of the data module 7, a display module 8 connected to it is provided on the holding device 2. The display module or the display device 8 allows the user, for example a physician, to view the results of the measurements carried out with the aid of the microneedle array 3 and to do so practically in real time. In the illustrative embodiment, the holding device 2 for securing the microneedle array 3 is identical to the one for receiving the display module 8, that is to say designed as a glove, in this case with the display module 8 arranged on the back of the glove. In alternative embodiments, the holding device 2 is designed in a number of parts.

In addition to the display of data generated in the data module 7, there is also a link between the data module 7 and a dosing unit 9. The data link, which can be realized in any desired manner, for example as a radio link in a network within which data from the electronic patient record EPR are also transmitted, is symbolized in FIG. 1 as a broken line, like the other data links mentioned above. The dosing unit 9 serves to administer a medicament to the patient as a function of the measurement results evaluated in the data module 7, and taking into account the electronic patient record EPR. The microneedle array 3 for collecting the sample is coupled to the dosing unit 9 to form a closed-loop system.

Because the microneedle array 3 is easy to handle, the diagnostic article 1 is also particularly suitable for self-testing, for example in the case of diabetes patients, as so-called monitoring device. By using the diagnostic article 1, the diagnosis is personalized, as the direct personal contact is part of the diagnosis process. The display module 8 integrated in the holding device 2 or supported by it additionally permits rapid reaction to the measurement result obtained with the aid of the microneedle array 3.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A diagnostic article, comprising:
   a microneedle array;
   a holding device, adapted to support the microneedle array;
   a data recording device connected to the microneedle array;
   a data evaluation device connected to the data recording device; and
   a display device arranged on the holding device and connected to said data evaluation device, wherein the holding device is a glove.

2. The diagnostic article as claimed in claim 1, wherein a dosing article is connectable to the data evaluation device.

3. The diagnostic article as claimed in claim 2, wherein needles of the microneedle array are a maximum of 2 mm in height.

4. The diagnostic article as claimed in claim 2, wherein needles of the microneedle array include a fluid channel with an internal diameter of a maximum of 150 μm.

5. The diagnostic article as claimed in claim 4, wherein needles of the microneedle array are a maximum of 2 mm in height.

6. The diagnostic article as claimed in claim 2, wherein the data evaluation device is linked to an electronic patient record.

7. The diagnostic article as claimed in claim 1, wherein needles of the microneedle array are a maximum of 2 mm in height.

8. The diagnostic article as claimed in claim 7, wherein needles of the microneedle array include a fluid channel with an internal diameter of a maximum of 150 µm.

9. The diagnostic article as claimed in claim 7, wherein the data evaluation device is linked to an electronic patient record.

10. The diagnostic article as claimed in claim 1, wherein needles of the microneedle array include a fluid channel with an internal diameter of a maximum of 150 µm.

11. The diagnostic article as claimed in claim 1, wherein the data evaluation device is linked to an electronic patient record.

12. The diagnostic article as claimed in claim 11, wherein needles of the microneedle array are a maximum of 2 mm in height.

13. The diagnostic article as claimed in claim 11, wherein needles of the microneedle array include a fluid channel with an internal diameter of a maximum of 150 µm.

14. A diagnostic article, comprising; a microneedle array; means for supporting the microneedle array, wherein the means for supporting includes a glove; means for recording data obtained from the microneedle array; means for evaluating the recorded data, wherein said means for evaluating is integrated into the glove; and means for displaying data, wherein said means for displaying data is arranged on the glove.

15. The diagnostic article as claimed in claim 14, wherein a dosing article is connectable to the means for evaluating.

16. The diagnostic article as claimed in claim 14, wherein needles of the microneedle array are a maximum of 2 mm in height.

17. The diagnostic article as claimed in claim 14, wherein needles of the microneedle array include a fluid channel with an internal diameter of a maximum of 150 µm.

18. The diagnostic article as claimed in claim 14, wherein the means for evaluating is linked to an electronic patient record.

* * * * *